United States Patent [19]

Antrim et al.

[11] Patent Number: 5,322,778
[45] Date of Patent: Jun. 21, 1994

[54] LIQUEFACTION OF GRANULAR STARCH SLURRIES USING AN ANTIOXIDANT WITH ALPHA AMYLASE

[75] Inventors: Richard L. Antrim, Hawthorne, Ill.; Leif P. Solheim, Clinton, Iowa

[73] Assignee: Genencor International, Inc., Rochester, N.Y.

[21] Appl. No.: 785,624

[22] Filed: Oct. 31, 1991

[51] Int. Cl.$^5$ .................. C12P 19/14; C12N 9/24; C12N 9/26; C12N 9/28
[52] U.S. Cl. ............................. 435/99; 435/201; 435/202; 435/203; 435/204; 435/275
[58] Field of Search ............... 435/99, 201, 202, 203, 435/179, 267

[56] References Cited

U.S. PATENT DOCUMENTS

| | | | |
|---|---|---|---|
| 4,111,750 | 9/1978 | Colilla et al. | 435/276 |
| 4,284,722 | 8/1981 | Tamuri | 435/94 |
| 4,376,824 | 3/1983 | Huest et al. | 435/94 |
| 4,405,648 | 9/1983 | Atsumi et al. | 435/201 |
| 4,647,538 | 3/1987 | Zeikus et al. | 435/105 |
| 4,774,183 | 9/1988 | Fan | 435/19 |
| 4,933,279 | 6/1990 | Carroll et al. | 435/42 |
| 5,084,385 | 1/1992 | Ashikari et al. | 435/96 |

FOREIGN PATENT DOCUMENTS 0189838 8/1986 European Pat. Off. .

OTHER PUBLICATIONS

Cleland, (1964) "Dithiothreitol, A New Protective Reagent for SH Groups," *Biochemistry* 3:1.
Watson, (1967) *Starch: Chemistry & Technology*, vol. II, *Industrial Aspects*, Academic Press pp. 30–51.
Aschengreen, et al., (1979) *Starch* 31:64–66.
Alexander, R., (1987) "Corn Dry Milling: Processes, Products, and Applications," Chp. 11 of *Corn: Chemistry & Technology*, pp. 351–376.
*Standard Analytical Methods of the Member Companies of the Corn Refiners Association, Inc.*, 6th Ed.
Kirk-Othmer, 3rd Ed., (1978) "Antioxidants and Antiozonants," vol. 3, pp. 128–148.

*Primary Examiner*—Douglas W. Robinson
*Assistant Examiner*—L. Blaine Lankford

[57] ABSTRACT

The present invention relates to a process of liquefying starch wherein the liquefaction step is carried out at pH less than 6. It also relates to the use of antioxidants.

11 Claims, No Drawings

LIQUEFACTION OF GRANULAR STARCH SLURRIES USING AN ANTIOXIDANT WITH ALPHA AMYLASE

FIELD OF THE INVENTION

The present invention relates to the liquefaction of grain starch in the production of dextrose, fructose, alcohol and the like at pH's less than 6 using alpha amylase. It also relates particularly to the addition of an antioxidant to the process to reduce liquefaction time and consistently achieve adequate liquefaction at below pH 6.

BACKGROUND INFORMATION

Grains such as corn have long been used as a source of starch. One of the classic methods of separating the starch and then using it in other industrial processes is the wet-milling process. This method is a highly specific and integrated system developed to separate the major components of a grain kernel as completely as possible (see Stanley A. Watson, *Starch: Chemistry & Technology*, Vol. II, *Industrial Aspects*, Academic press, New York, 1967, pp 30–51). A final granular starch slurry coming out of the wet milling process can be used in a variety of industrial processes.

One of the most important processes is the conversion of starch to high fructose syrup. In practice, this conversion involves four major steps; namely liquefaction of granular starch slurry, saccharification of the liquified starch into dextrose, purification, and then isomerization of dextrose into fructose. The most common grain used in this process is corn in the production of high fructose corn syrup (see N. H. Aschengreen, et al; *Starch* Vol. 31, pp 64–66 (1979)). During the four step conversion to fructose, it is currently necessary that the granular starch slurry is varied widely in pH. The pH of the slurry coming out of the commercial wet-milling operation is about 4, then raised to a pH of from 6–6.4, and calcium is added along with enzyme. For saccharification of the starch the ph is lowered to 4.3–4.5 and for the final isomerization the pH is increased back to about 7.8. The result of these wide shifts in pH is a high ion exchange requirement to desalt the syrup during and after processing. Furthermore, high pH causes by-product formation, sugar breakdown, color formation, and an overall decrease in product yield. These factors add millions of dollars annually to the cost of high fructose syrup production. The industrial isomerization process is currently very efficient due to current processing techniques and the short processing time. Accordingly, it would be useful if the liquefaction step could be carried out at lower pH's to obviate the need for a pH shift in commercial processes. It is possible to perform liquefaction at pH's less than 6 (see e.g. U.S. Pat. No. 4,376,824); however, the liquefaction is sometimes unexplainably incomplete and so has limited commercial utility. The antioxidant bisulfite has been used in the past as a component of starch slurry that is added during steeping operations to control pH and the nature of the fermentation. It is normally removed with the steep liquor.

Another source of starch is from the dry milling process. In the dry milling process the grain is ground and liquefaction can be carried on with or without separation of individual components of the kernel into grits, cornmeal or flour (see e.g. Corn: Chemistry & Technology by Alexander, K., 1987, Chap. 11, Corn Dry Milling Productions and Applications). In addition to uses as in a variety of food and feed stuffs, he grain can also be used in the conversion of starch to alcohol. This process involves two steps to convert the milled grain or fractions therefrom into alcohol: liquefaction of the starch in the dry products after addition of water, and most generally a combined or simultaneous saccharification of the starch into glucose and fermentation of the glucose into alcohol.

The natural pH of the starch slurry of about 5 is adjusted upward with alkali or carbonate to a pH of 6.2–6.4 for liquefaction. After liquefaction the pH is adjusted downward by addition of acid or "backset" from previous fermentations. There are disadvantages to use of "backset" such as introduction of microbial contaminants into the fermentation.

The utility of the process of the invention is to reduce the need for pH adjustment on the up side and down side.

SUMMARY OF THE INVENTION

One method of liquefying a dry milled grain slurry at a pH of about 4 to less than 6 comprising (a) adding at least about 8 liquefons of alpha amylase per gram of starch to the slurry; (b) adding an effective amount of an antioxidant to the slurry to allow liquefaction; (c) reacting the slurry for the appropriate time and temperature to liquefy the starch.

DETAILED DESCRIPTION OF THE INVENTION

It has been discovered that when alpha amylase is added to a granular starch slurry at pH's less than 6 in the presence of at least about 5 mM of an antioxidant, a satisfactory liquefaction can be achieved.

As used herein "granular starch slurry" refers to any of the various edible grains which have been wet milled and water added to produce a starch slurry ("dry milled grain slurry" refers to any of the same grains which have been dry ground into grits, flour, meal, etc., and water added to produce a slurry). Examples of edible starch containing grains include corn, wheat, milo and the like. Typically, the dry starch component is roughly between about 25% and 40% on a weight basis of the slurry with the examples herein adjusted to 35% starch.

The enzyme used herein for addition to the slurry is alpha amylase. Alpha amylase is an endo-amylolytic enzyme capable of promoting random cleavage of $\alpha$-1,4 glucosidic bonds within the starch molecule and is produced by a number of types of microorganisms such as members of Bacillus and Aspergillus. Especially preferred are alpha amylase enzymes derived from *Bacillus licheniformis, B. subtilis* and *B. stearothermophilus*. Enzyme activity is measured in a unit called the liquefon. In the practice of the invention, at least about 8 liquefons of alpha amylase activity are used per dry gram of starch present in the slurry. Typically the amount is from about 10–20 liquefons/g, preferably 12–14 liquefons/g, although were a faster result is desired, more alpha amylase may be added.

Antioxidants are a well known class of compounds (see e.g. Kirk & Othmer 3rd Edition, Vol. 3 "Antioxidants and Antiozonants"), and enjoy use in a wide variety of products including rubber, plastics, foodstuffs, animal feed, etc. Until now, however, they have not been used to control useful pH in the liquefaction of starch. Important types include amines, phenols, phosphites, sulfides, metal salts of dithioacids, etc. Major antioxidants known to be suitable for food use include ascorbic acid, sodium ascorbate, calcium ascorbate, ascorbyl palmitate, BHA, BHT, erthorbic acid, propionic acid, dilauryl thiodipropionate, TBHQ and a host of others. With concern in today's environment about additives in food there is a constant attempt at developing new antioxidants. Preferred antioxidants in this application include bisulfites (sodium metabisulfite or sodium bisulfite), sodium ascorbate, BHT, 3,3'-thiodipropionic acid and the like.

Some antioxidants would not be acceptable, however. Those unacceptable ones would be those which are incompatible with alpha amylase. This could be because of direct inhibition of the enzyme, inactivation or degradation of the enzyme by the antioxidant. One skilled in the art would be able to readily tell which antioxidants would be non-compatible, or at the very least, run a sample test such as in Example 9 to determine which ones act this way.

The liquefaction may be carried out in a one-stage or conventional two-stage process. In a two-stage process alpha amylase is added to a slurry, and the slurry is first held at 100°–105° C. for a period of about 2–10 minutes. Next, the temperature is reduced to about 90°–100° C. and held up to 120 minutes, preferably no greater than 90 minutes.

Starch liquefaction processes are generally carried out in the presence of calcium to impart heat stability to the enzyme. Various alpha amylases have differing heat stabilities and so somewhere between 20 ppm and 200 ppm is added. Calcium in the form of lime has frequently been used for this purpose wherein it also serves to help adjust pH levels upward from the initial low pH of the fresh starch slurry. In general it is desirable that calcium levels be under 100 ppm, due in part to incompatibility to the downstream isomerization process and demands in ion-exchange refining.

The present invention maintains the reaction at a pH of less than about 6 to about 4.5 during liquefaction. The preferred pH is as close to 4.5 as possible but preferably about 4.5–5.2. Calcium compounds, e.g. lime or calcium carbonate, are commonly used to adjust the pH upward from the initial pH of the granular starch during liquefaction. Other compounds used to adjust the pH upward include sodium hydroxide and sodium carbonate.

In the practice of the invention a key unobvious and novel aspect of the liquefaction process taught herein is the addition of an effective amount, normally at least 5 mM of antioxidant, preferably from about 10 mM to about 80 mM, more preferably from about 20 mM to about 40 mM. As mentioned above, normally enough buffer is added to adjust the pH up from 4 to the desired pH less than 6, preferably around 5, or as low as possible. The applicants have found that the antioxidant allows complete liquefaction in reasonable periods of time at lower pH values compared with those processes without antioxidant.

The result of using the process herein in the presence of antioxidant is that we gain two-fold, namely, the process can be carried out at a lower pH than would otherwise be possible per given time. Further, the resultant slurry will have little or no raw starch remaining with a Dextrose Equivalent (DE) of about 10 or less.

The following examples are representative of the invention. One skilled in the art would be able to substitute conditions, wet or dry milled grains, temperatures, enzymes, antioxidant sources and the like and are intended only as instructive as well as representative of best mode.

EXAMPLE 1

Alpha Amylase Activity Determination

The sample illustrates a method for the determination of alpha-amylase activity.

The determination of alpha-amylase activity is based upon the ability of native starch to form a blue colored complex with iodine, and the disappearance of this color when starch is hydrolyzed into shorter dextrin molecules. The alpha amylase activity was defined in terms of the digestion time required to produce a color change denoting a definite state of dextrination of the starch.

Reagents

Phosphate buffer—Sodium hydroxide (25.3 g) and potassium dihydrogen phosphate (340 g) were dissolved in water and diluted to approximately 2 liters. The buffer was cooled to room temperature and the pH adjusted to $6.2\pm0.1$. The buffer was diluted to 2 liters in a volumetric flask.

Starch substrate—Ten grams (dry substance) of soluble Lintner Starch were suspended in 50 ml of water and washed into approximately 300 ml of boiling water. The suspension was again brought to boiling and boiled for 5 minutes with constant stirring. The starch solution was cooled with constant stirring to room temperature and 125 ml of phosphate buffer were added. The solution was diluted to 500 ml with water. The starch substitute was made fresh daily.

Stock iodine solution—Iodine crystals (5.5 g) and potassium iodide (11.0 g) were dissolved in water and volumetrically diluted to 250 ml. The solution was kept from light.

Dilute iodine solution—Potassium iodide (20 g) and 2 ml of stock iodine solution were dissolved in water and diluted volumetrically to 500 ml. The solution was made fresh daily.

Enzyme dilution solution—Calcium chloride (11.1 g) was dissolved in 4 liters of water.

Water used for all reagents was either distilled or deionized.

Apparatus

Constant temperature bath set at 30° C.$\pm$0.2° C. Hellige comparator equipped with a special alpha amylase color disc (catalog number 620-S5). Precision bore 13 mm square tubes from Hellige Inc. One and five milliliter automatic pipets.

Procedure

The unknown alpha amylase sample was diluted to b 10–15 LU/ml (as defined below) with the enzyme diluting solution. For many commercial alpha amylase preparations a suitable dilution was found to be 2000.

Five milliliter aliquots of dilute iodine solution were dispensed into 13$\times$100 mm test tubes and 10 ml of starch solution was placed in a 23$\times$200 test tube and all tubes were attemperated in the 30° C. water bath.

Five milliliters of diluted enzyme solution (also at 30° C.) were mixed with the starch solution and timing was begun. At appropriate time intervals, 1 ml aliquots of the hydrolyzing mixture were transferred to a test tube containing the attemperated diluted iodine solution. The starch-iodine solution was mixed and transferred to a 13 mm precision tube and the color was compared with the standard alpha amylase color disc in the Hellige comparator. When the time of the end point was approached, samples were taken at 0.25 minute intervals.

The time required for the colors of the samples and the color disc to match were recorded and the activity in Liquefons per gram or ml was calculated according to the formula:

$$LU/ml \text{ or } LU/g = \frac{570}{V \times t} \times D$$

Where
LU = liquefon unit
V = volume of sample (5 ml)
t = dextrinization time (minutes)
D = dilution factor = dilution volume/ml or g of added enzyme.

EXAMPLE 2

Starch Liquefaction Conditions Determination of Liquefied Starch DE

This sample describes the process for the liquefaction of starch using a jet cooker.

Starch liquefaction was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90-100 psi. Temperature probes were installed just after the Hydroheater jet and just before the back pressure valve.

Starch slurry was typically obtained from a corn wet miller and used within two days. The starch was diluted to the desired solids level with deionized water and the pH of the starch was adjusted with 2% NaOH or saturated $Na_2CO_3$. Typical liquefaction conditions were:

Starch 32%-35% solids
Calcium 35-45 ppm (25 ppm added)
pH 5.0-6.0
Alpha amylase 12-14 LU/g starch dry basis Starch was introduced into the jet at about 500 ml/min. The jet temperature was held at 103° C.-105° C. Samples of starch were transferred from the jet cooker to a 95° C. second stage liquefaction bath and held for 90 minutes.

The degree of starch liquefaction was measured immediately after the second stage liquefaction by determining the dextrose equivalence (DE) of the sample and by testing for the presence of raw starch, both according to the methods described in the *Standard Analytical Methods of the Member Companies of the Corn Refiners Association, Inc.*, sixth edition. Starch, when treated generally under the conditions given above and at pH 6.0, will yield a liquefied starch with a DE of about 10 and with no raw starch.

EXAMPLE 3

Effect of Bisulfite on DE of Starch Liquified at pH 5.2

This example demonstrates the effect on DE when liquefying cornstarch in the presence of bisulfite ion at lower than conventional pH.

A cornstarch slurry obtained from a corn-wetmilling plant was diluted to 35% dry solids with deionized water, and 30 ppm calcium ion was added as $CaCl_2$. The pH of the slurry was adjusted to about 5.2 with 2.5% NaOH. Bisulfite ion was added to aliquots as sodium metabisulfite to provide levels of 5, 20 and 40 millimolar. Alpha amylase produced by a strain of *Bacillus licheniformis* and available commercially as SPEZYME® AA-20 from Genencor International, Inc. was added at a dosage of 12 liquefons/gram starch dry basis. The pH was readjusted to 5.20 with 2.5% NaOH.

The starch slurries which were maintained in suspension by overhead stirring, were introduced into a steam jet at 500 ml/min as described in Example 2. The jet temperature was held at 103° C.-105° C. by controlling the steam flow and maintaining back pressure at ~4 PSIG. Samples of cooked starch were transferred from the jet cooker to a 95° C. second stage liquefaction bath and held for 90 minutes.

The degree of starch liquefaction and presence of raw starch were measured immediately after the second stage as described in Example 2. The following Table illustrates the effect of bisulfite ion on development of DE. Satisfactory DE values and absence of raw starch were achieved at pH 5.2 at bisulfite levels greater than about 20 mM.

| EFFECT OF BISULFITE ON STARCH LIQUEFACTION AT pH 5.2 | | |
|---|---|---|
| Bisulfite Level (mM) | DE | Raw Starch |
| 0 | 1.8 | + |
| 5 | 6.7 | + |
| 20 | 9.5 | − |
| 40 | 11.0 | − |

EXAMPLE 4

Effect of Time on DE Development at Various Bisulfite Concentrations

This example illustrates the rate of DE development during a 95° C. second-stage liquefaction as a function of bisulfite concentration. The example further illustrates that surprisingly the bisulfite is acting to stabilize the alpha amylase by unknown mechanisms during the first stage liquefaction as evidenced by the DE values being essentially the same immediately after the first stage but with different rates of liquefaction being obtained during the second stage of liquefaction.

Liquefaction was carried out as described in Example 3 except the DE determinations were done after 30, 60, 90 and 120 minutes of second-stage liquefaction. The following table illustrates that DE develops with time during second stage liquefaction when the enzyme is stabilized with bisulfite during first stage liquefaction. Bisulfite protects the enzyme so that more active enzyme is present during second stage liquefaction. If the effect of bisulfite were to super-activate the enzyme or to somehow cause the starch to be more accessible to the enzyme, then the primary effect would be in the short, first stage liquefaction and not in the second stage.

| EFFECT OF TIME ON DE DEVELOPMENT AT VARIOUS BISULFITE CONCENTRATIONS | | | | | |
|---|---|---|---|---|---|
| Bisulfite Concentration mM | 0 Min | 30 Min | 60 Min | 90 Min | 120 Min |
| 0 | 0.5 | 0.8 | 1.5 | 1.8 | 2.2 |
| 5 | 0.5 | 2.5 | 4.5 | 6.7 | 9.2 |
| 20 | 1.5 | 4.0 | 7.0 | 8.6 | 13.0 |

EXAMPLE 5

Effect of Bisulfite on D.E. of Starch Liquified at pH 4.5

This example demonstrates the effect on DE when liquefying cornstarch in the presence of bisulfite ion at a pH of 4.5—a full 1.5 pH units below convention pH, and that the alpha-amylase is active at pH 4.5.

A cornstarch slurry obtained from a corn-wetmilling plant was diluted to 35% dry solids with deionized water, and 30 ppm calcium was added as $CaCl_2$. The pH of the slurry was adjusted to about 4.5 with 2.5% NaOH. Bisulfite ion was added as sodium metabisulfite to provide a level of 80 millimolar. Alpha amylase produced by a strain of *Bacillus licheniformis* and available commercially as SPEZYME ® AA-20 from Genencor International, Inc. was added at a dosage of 16 liquefons/gram starch dry basis. The pH was readjusted to 4.50 with 2.5% NaOH or 5% HCl.

The starch slurry which was maintained in suspension by overhead stirring, was introduced into a steam jet at 500 ml/min. as described in Example 2. The jet temperature was held at 103° C.–105° C. by controlling the steam flow and maintaining back pressure at ~4 PSIG. A sample of cooked starch was transferred from the jet cooker to a 95° C. second stage liquefaction bath and held for 90 minutes.

The degree of starch liquefaction and presence of raw starch were measured immediately after the second stage as described in Example 2.

Control liquefactions were run in the same manner at pH's 4.5 and 5.2 with the exception that the 80 mM sodium bisulfite was omitted. The following table shows the unexpected benefit from added bisulfite even at a pH as low as 4.5.

| DE OF STARCH LIQUEFIED AT pH 4.5 | | |
|---|---|---|
| Bisulfite Level | DE | Raw Starch |
| 0 | ~0 | + |
| 80 mM | 10.05 | − |
| 0 (pH 5.2) | 2.0 | + |

EXAMPLE 6

Effect Of Ascorbate On DE of Starch Liquefied at pH 5.2

This example demonstrates the effect on DE when liquefying cornstarch in the presence of ascorbate ion at lower than conventional pH.

A cornstarch slurry obtained from a corn-wetmilling plant was diluted to 35% dry solids with deionized water, and 30 ppm calcium ion was added as $CaCl_2$. Ascorbate ion was added as ascorbic acid to provide a concentration of 40 millimolar. The pH of the slurry was adjusted to about 5.2 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to 5.20 with 2.5% NaOH or 5% HCl. A control slurry was prepared without addition of ascorbate.

The starch slurries, which were maintained in suspension by overhead stirring, were introduced into a steam jet at 500 ml/min as described in Example 2. The jet temperature was held at 103° C.–105° C. by controlling the steam flow and maintaining back pressure at 4 PSIG. Samples of cooked starch were transferred from the jet cooker to a 95° C. second stage liquefaction bath and held for 90 minutes.

The degree of starch liquefaction and presence of raw starch were measured immediately after the second stage as described in Example 2. The following Table illustrates the effect of ascorbate ion on development of DE. Satisfactory DE values and absence of raw starch were achieved at pH 5.2 at an ascorbate level of 40 mM.

| EFFECT OF ASCORBATE STARCH LIQUEFACTION AT pH 5.2 | | |
|---|---|---|
| Ascorbate Level (mM) | DE | Raw Starch |
| 0 | 1.4 | + |
| 40 | 10.5 | − |

EXAMPLE 6A

Effect Of Ascorbate On DE Of Starch Liquefied At pH 5.1 Is Concentration Dependent This example demonstrates the effect on DE when liquefying cornstarch in the presence of ascorbate ion at lower than conventional pH.

A cornstarch slurry obtained from a corn-wetmilling plant was diluted to 35% dry solids with deionized water, and 30 ppm calcium ion was added as $CaCl_2$. Ascorbate ion was added to the starch slurry as sodium ascorbate to provide concentrations of 2.5, 10, and 30 millimolar. The pH of the slurry was adjusted to about 5.1 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to 5.1 with 2.5% NaOH or 6% HCl. A control slurry was prepared without addition of ascorbate.

The starch slurries, which were maintained in suspension by overhead stirring, were introduced into a steam jet at 360 ml/min as described in Example 2. The jet temperature was held at 105° C.–107° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of ascorbate ion on development of DE. As the concentration of ascorbate ion increased, the development of DE increased.

| EFFECT OF ASCORBATE ON STARCH LIQUEFACTION AT pH 5.1 | | |
|---|---|---|
| Ascorbate Level (mM) | DE | Raw Starch |
| 0.0 | Too thick to measure | |
| 2.5 | 0.3 | + |
| 10.0 | 5.7 | + |
| 30.0 | 8.6 | + |

EXAMPLE 7

Effect Of BHT On DE Of Starch Liquefied At pH 5.2

This example demonstrates the effect on DE when liquefying cornstarch in the presence of BHT (Butylated Hydroxytoluene) at lower than conventional pH.

A cornstarch slurry obtained from a corn-wetmilling plant was diluted to 35% dry solids with deionized water, and 30 ppm calcium ion was added as CaCl$_2$. BHT was added to provide a concentration of 20 millimolar. The pH of the slurry was adjusted to about 5.2 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to 5.20 with 2.5% NaOH or 5% HCl. A control slurry was prepared without addition of BHT.

The starch slurries, which were maintained in suspension by overhead stirring, were introduced into a steam jet at 500 ml/min as described in Example 2. The jet temperature was held at 103° C.–105° C. by controlling the steam flow and maintaining back pressure at 4 PSIG. Samples of cooked starch were transferred from the jet cooker to a 95° C. second stage liquefaction bath and held for 90 minutes.

The degree of starch liquefaction and presence of raw starch were measured immediately after the second stage as described in Example 2. The following Table illustrates the effect of BHT on development of DE. A higher DE value and absence of raw starch were achieved at pH 5.2 at a BHT level of 20 mM.

| EFFECT OF BHT ON STARCH LIQUEFACTION AT pH 5.2 | | |
|---|---|---|
| BHT Level (mM) | DE | Raw Starch |
| 0 | 3.1 | + |
| 20 | 7.7 | − |

EXAMPLE 8

Effect Of 3,3'-Thiodipropionic Acid On The DE Of Starch Liquefied At pH 5.1

This example demonstrates the effect on DE when liquefying cornstarch in the presence of 3,3'-thiodipropionic acid at lower than conventional pH.

A cornstarch slurry obtained from a corn-wetmilling plant was diluted to 35% dry solids with deionized water, and 30 ppm calcium ion was added as CaCl$_2$. 3,3'-Thiodipropionic acid was added to the starch slurry to provide a concentration of 40 millimolar. The pH of the slurry was adjusted to about pH 5.1 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. A control slurry was prepared without addition of 3,3'-thiodipropionic acid.

The starch slurries, which were maintained in suspension by overhead stirring, were introduced into a steam jet at 360 ml/min as described in Example 2. The jet temperature was held at 105° C.–107° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of 3,3'-thiodipropionic acid on development of DE. Satisfactory DE values and an absence of raw starch were achieved at a 3,3'-thiodipropionic acid concentration of 40 mM.

| EFFECT OF 3,3'-THIODIPROPIONIC ACID ON STARCH LIQUEFACTION AT pH 5.1 | | |
|---|---|---|
| 3,3'-Thiodipropionic Acid (millimolar) | DE | Raw Starch |
| 0 | Too thick to measure, DE < 1 | |
| 40 | 9.9 | − |

EXAMPLE 9

Ineffectiveness Of Some Antioxidants Which Interfere With Alpha Amylase On DE of Starch Liquefied At pH 5.2

This example demonstrates the lack of an effect on DE when liquefying cornstarch in the presence of propyl gallate or β-mercaptoethanol at lower than conventional pH.

A cornstarch slurry obtained from a corn-wetmilling plant was diluted to 35% dry solids with deionized water, and 30 ppm calcium ion was added as CaCl$_2$. Propyl gallate was added to the starch slurry to provide a concentration of 20 millimolar or β-mercaptoethanol was added to the starch slurry to provide a concentration of 40 millimolar. The pH of the slurry was adjusted to about pH 5.2 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to 5.2 with 2.5% NaOH or 6% HCl. Control slurries were prepared without addition of either propyl gallate or β-mercaptoethanol.

The starch slurries, which were maintained in suspension by overhead stirring, were introduced into a steam jet at 500 ml/min as described in Example 2. The jet temperature was held at 103° C.–105° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of propyl gallate and β-mercaptoethanol on development of DE. Both propyl gallate and β-mercaptoethanol caused a decrease in DE development over the control reaction containing no added antioxidant.

| EFFECT OF PROPYL GALLATE OR β-MERCAPTOETHANOL ON STARCH LIQUEFACTION AT pH 5.2 | | |
|---|---|---|
| Antioxidant Level | DE | Raw Starch |
| 0 | 3.1 | + |
| 20 mM Propyl Gallate | 0.8 | + |
| 0 | 6.1 | + |
| 40 mM β-Mercaptoethanol | 3.6 | + |

EXAMPLE 10

The Effect Of Bisulfite On DE Of Liquefied Starch Is pH Dependent

This example demonstrates that the effect on DE when liquefying cornstarch in the presence of bisulfite is dependent on the pH of the liquefaction.

A cornstarch slurry obtained from a corn-wetmilling plant was diluted to 35% dry solids with deionized water, and 30 ppm calcium ion was added as CaCl$_2$. Bisulfite ion was added as Na$_2$S$_2$O$_5$ to the starch slurry to provide concentrations of 5, 15 and 40 millimolar. For each bisulfite concentration, three starch slurries were prepared and the pH adjusted to about 5.9, 5.5 or 5.1 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to the desired pH ( 5.9, 5.5 or 5.1) with 2.5% NaOH or 6% HCl. A control slurry was prepared at each pH without addition of bisulfite ion.

The starch slurries, which were maintained in suspension by overhead stirring, were introduced into a steam jet at 360 ml/min as described in Example 2. The jet temperature was held at 105° C.–107° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of bisulfite ion on development of DE. As the pH of the starch slurry decreased from 5.9 to 5.1 the effect of bisulfite on DE of the liquefied starch increased.

| EFFECT OF BISULFITE ON STARCH LIQUEFACTION AT pH 5.9, 5.5 OR 5.1 | | | |
|---|---|---|---|
| Bisulfite Level (mM) | pH | DE | Raw Starch |
| 0 | 5.9 | 9.5 | — |
| 5 | 5.9 | 10.5 | — |
| 15 | 5.9 | 11.0 | — |
| 40 | 5.9 | 11.6 | — |
| 0 | 5.5 | 4.5 | + |
| 5 | 5.5 | 8.4 | + |
| 15 | 5.5 | 11.6 | — |
| 40 | 5.5 | 11.2 | — |
| 0 | 5.1 | <0.5 | + |
| 5 | 5.1 | 4.6 | + |
| 15 | 5.1 | 8.7 | + |
| 40 | 5.1 | 9.2 | — |

EXAMPLE 11

The Effect of Ascorbate On DE Of Liquefied Starch Is pH Dependent

This example demonstrates that the effect on DE when liquefying cornstarch in the presence of ascorbate is dependent on the pH of the liquefaction.

A cornstarch slurry obtained from a corn-wetmilling plant was diluted to 35% dry solids with deionized water, and 30 ppm calcium ion was added as CaCl$_2$. Ascorbate ion was added as sodium ascorbate to the starch slurry to provide a concentration of 2.5, 10 and 30 millimolar. For each ascorbate ion concentration, three starch slurries were prepared and the pH the adjusted to about 5.9, 5.5 or 5.1 with 2.5% NaOH. Alpha amylase produced by a strain of *Bacillus licheniformis* and available commercially as SPEZYME ® AA-20 from Genencor International, Inc. was added at a dosage of 12 liquefons/gram starch dry basis. The pH was readjusted to the desired pH (5.9, 5.5 or 5.1) with 2.5% NaOH or 6% HCl. A control slurry was prepared at each pH without addition of ascorbate ion.

The starch slurries, which were maintained in suspension by overhead stirring, were introduced into a steam jet at about 360 ml/min as described in Example 2. The jet temperature was held at 105° C.–107° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of ascorbate ion on development of DE. As the pH of the starch slurry decreased from 5.9 to 5.1 the effect of ascorbate ion on DE of the liquefied starch increased.

| EFFECT OF ASCORBATE ON STARCH LIQUEFACTION AT pH 5.9, 5.5 OR 5.1 | | | |
|---|---|---|---|
| Ascorbate Level (mM) | pH | DE | Raw Starch |
| 0 | 5.9 | 10.3 | — |
| 2.5 | 5.9 | 10.6 | — |
| 10 | 5.9 | 11.5 | — |
| 30 | 5.9 | 12.1 | — |
| 0 | 5.5 | 6.2 | + |
| 2.5 | 5.5 | 7.8 | + |
| 10 | 5.5 | 9.4 | — |
| 30 | 5.5 | 11.9 | — |
| 0 | 5.1 | <0.1 | + |
| 2.5 | 5.1 | 0.3 | + |
| 10 | 5.1 | 5.7 | + |
| 30 | 5.1 | 8.6 | + |

EXAMPLE 12

Effect of Bisulfite On DE Of Starch Liquefied By Alpha Amylase From *Bacillus stearothermophilus* at pH 5.0

This example demonstrates the effect on DE when liquefying cornstarch with α-amylase from *Bacillus stearothermophilus* in the presence of bisulfite ion at lower than conventional pH.

A cornstarch slurry obtained from a corn-wetmilling plant was diluted to 35% dry solids with deionized water, and 30 ppm calcium ion was added as CaCl$_2$. Bisulfite ion was added to the starch slurry as Na$_2$S$_2$O$_5$ to provide a concentration of 40 millimolar. The pH of the slurry was adjusted to about pH 5.0 with 2.5% NaOH. Alpha amylase produced by a strain of *Bacillus stearothermophilus* and available commercially as G-ZYME ™ G995 from Enzyme Bio-Systems Ltd. was added at a dosage of 12 liquefons/gram starch dry basis. The pH was readjusted to 5.0 with 2.5% NaOH or 6% HCl. A control slurry was prepared without addition of bisulfite.

The starch slurries, which were maintained in suspension by overhead stirring, were introduced into a steam jet at 360 ml/min as described in Example 2. The jet temperature was held at 105° C.–107° C. by controlling the steam flow and maintaining back pressure at 4 psig. Samples of cooked starch were transferred from the jet cooker to a 95° C. second stage liquefaction bath and held for 90 minutes.

The degree of starch liquefaction was measured immediately after the second stage as described in Example 2. The following Table illustrates the effect of bisulfite on development of DE. Bisulfite acts to improve the DE development on starch liquefied with α-amylase from *Bacillus stearothermophilus* as well as α-amylase from *Bacillus licheniformis*.

| EFFECT OF BISULFITE ON STARCH LIQUEFACTION AT pH 5.0 USING α-AMYLASE FROM *Bacillus stearothermophilus* | | |
|---|---|---|
| Bisulfite Level (millimolar) | DE | Raw Starch |
| 0 | 2.6 | + |
| 40 | 20.1 | − |

What is claimed is:

1. A method of liquefying a granular starch slurry from either a wet or dry milling process at a pH of about 4 to less than 6 comprising the steps of:
   (a) adjusting the pH of the starch slurry to about 4 to less than 6;
   (b) adding in either order at least about 8 liquefon units of microbial alpha amylase per gram of starch to the slurry, and at least 5 mM of an antioxidant to the slurry to allow liquefaction wherein said antioxidant is selected from the group consisting of bisulfites and salts thereof, ascorbic acid and salts thereof, sulfides, the phenolic antioxidants consisting of butylated hydroxyanisole, butylated hydroxytoluene and α-tocopherol, and erythorbic acid and salts thereof; and
   (c) reacting the slurry for the appropriate time and temperature to liquefy the starch wherein said temperature of the slurry is from about 100° C. to about 107° C. for an initial period and then the slurry is held at a temperature from about 90° C. to about 100° C.

2. A method according to claim 1 wherein the bisulfite is added in an amount at least about 30 millimolar.

3. A method according to claim 1 wherein the slurry is reacted in step c) at a temperature from about 100° C. to about 105° C. for an initial period and then the slurry is held at a temperature from about 90° C. to about 100° C. for a length of time sufficient to liquefy the starch.

4. A method according to claim 1 wherein the ascorbic acid or salt thereof is added in an amount of at least about 40 millimolar.

5. A method according to claim 1 wherein the butylated hydroxytoluene is added in an amount of at least about 20 millimolar.

6. A method according to claim 1 wherein said sulfide is 3,3'-thiodipropionic acid.

7. A method according to claim 1 wherein the 3,3'-thiodipropionic acid is added in an amount of at least about 40 millimolar.

8. A method according to claim 1 wherein the alpha-amylase is selected from the group consisting of alpha-amylase enzymes derived from *Bacillus licheniformis, B. subtilis* and B. stearothermophilus.

9. The method according to claim 1 wherein the pH of the solution is about 4.5 to 5.2

10. The method according to claim 1 wherein the antioxidant is added to a concentration of at least 20 millimolar.

11. The method according to claim 1 wherein the reaction is run until the Dextrose Equivalents is at least about 10.

* * * * *